United States Patent
Van Soest

(10) Patent No.: US 7,474,392 B2
(45) Date of Patent: Jan. 6, 2009

(54) INSPECTION DEVICE FOR OBJECTS WITH A SPHERICAL SURFACE

(75) Inventor: Robert Van Soest, Ede (NL)

(73) Assignee: Staalkat International B.V., Aalten (NL)

( * ) Notice: Subject to any disclaimer, the term of this patent is extended or adjusted under 35 U.S.C. 154(b) by 115 days.

(21) Appl. No.: 10/577,286

(22) PCT Filed: Sep. 21, 2004

(86) PCT No.: PCT/NL2004/000655

§ 371 (c)(1),
(2), (4) Date: Apr. 24, 2006

(87) PCT Pub. No.: WO2005/045406

PCT Pub. Date: May 19, 2005

(65) Prior Publication Data

US 2007/0030669 A1    Feb. 8, 2007

(30) Foreign Application Priority Data

Oct. 24, 2003    (NL) .................................... 1024619

(51) Int. Cl.
*A01K 43/00* (2006.01)
(52) U.S. Cl. ............................. 356/52; 356/64; 356/66; 356/55
(58) Field of Classification Search ............. 356/52–68, 356/237.1–237.6
See application file for complete search history.

(56) References Cited

U.S. PATENT DOCUMENTS

| 1,947,142 | A | * | 2/1934 | Ward et al. ................ 356/237.1 |
| 5,201,576 | A | | 4/1993 | Squyres |
| 5,321,491 | A | * | 6/1994 | Summers et al. ............... 356/53 |

FOREIGN PATENT DOCUMENTS

| EP | 0 377 478 A1 | 7/1990 |
| JP | 58070150 A | 4/1983 |
| JP | 0805563 A | 1/1996 |
| JP | 08304290 A | 11/1996 |
| JP | 11101689 A | 4/1999 |
| JP | 200083926 A | 10/2000 |

OTHER PUBLICATIONS

English translation of JP 08-005563.
English translation of JP 11-101689.

(Continued)

*Primary Examiner*—Gregory J Toatley, Jr.
*Assistant Examiner*—Tri T Ton
(74) *Attorney, Agent, or Firm*—Hoffmann & Baron, LLP

(57) ABSTRACT

A device (1) for inspecting objects with a substantially spherical surface, such as for example eggs or fruit, comprises optical observation means (8) for observing the objects. The device has a supporting surface (10) for supporting the objects. There is a light source for illuminating the objects. The device also comprises a box (2) with reflective walls (3a, 4b and 4a shown) which is positioned above the supporting surface (11). The light source and the observation means (8) are accommodated in the box (2). A plurality of objects can be placed next to one another on the supporting surface (10) and can be illuminated equally well.

10 Claims, 4 Drawing Sheets

OTHER PUBLICATIONS

Linderhof—Wikipedia, the free encyclopedia (5 pages), http://en.wikipedia.org/wiki/Linderhof.

Bavarian Palace Department, Linderhof Palace and Park, Palace, History (3 pages), http://www.schlosslinderhof.de/englisch/palace/history.htm.

Bavarian Palace Department, Linderhof Palace and Park, Palace, Tour on the palace (1 page), http://www.schlosslinderhof.de/englisch/palace/rooms.htm.

Bavarian Palace Department, Linderhof Palace and Park, Palace, Tour on the palace, Hall of Mirrors (1 page), http://www.schlosslinderhof.de/englisch/palace/pict11.htm.

* cited by examiner

INSPECTION DEVICE FOR OBJECTS WITH A SPHERICAL SURFACE

CROSS-REFERENCE TO RELATED APPLICATIONS

This application is the National Stage of International Application No. PCT/NL2004/000655, filed Sep. 21, 2004, which claims the benefit of Netherlands Application No. NL 1024619, filed Oct. 24, 2003, the contents of which are incorporated by reference herein.

FIELD OF THE INVENTION

The invention relates to a device for inspecting objects with a substantially spherical surface, such as for example eggs or fruit, comprising optical observation means for observing the objects, a supporting surface for supporting the objects and a light source for illuminating the objects.

BACKGROUND OF THE INVENTION

When inspecting objects by means of optical observation means, the illumination of the objects is very important for the results of the inspection. In general, it is desirable for shadowing caused by non-uniform illumination, for example during the inspection of the surface of round objects, to be avoided. Shadows may be incorrectly regarded by the optical observation means as dirt or irregularities, which is deleterious to the inspection.

A device of this type is known. WO 03/023455 has disclosed a device in which light sources are positioned obliquely above and next to a conveyor in order to provide uniform illumination of the objects over the entire region in which the observation means observe the objects. The known device may have a plurality of conveyors arranged next to one another, in which case light sources are arranged next to and obliquely above each conveyor. In this case, light sources of a conveyor also illuminate the adjacent conveyor. In the known device, the light sources have to be positioned accurately in order to obtain uniform illumination of the objects. Furthermore, sufficient light sources per conveyor have to be provided. Furthermore, this arrangement of the light sources next to the conveyor means that only one or two objects can be placed next to one another on a conveyor to achieve good illumination.

Another device of the type referred to in the preamble is known from FR 2 699 696. This known device can be used, for example, to inspect the ripeness of fruit. The device comprises a box which is positioned above a reference plane. The reference plane may be moveable, so that objects are transported through the box. A ring of a transparent material is arranged approximately halfway up the height of the box. A light source which radiates light into the ring through an opening in the box is arranged outside the box. The ring transmits the light and is responsible for uniform illumination of the object, which is located beneath it approximately in the centre. An optical observation means is arranged in the top of the box for observing objects. The optical observation means as it were look at the object through the central opening in the ring. This known device is designed to illuminate and observe one object each time and is therefore not suitable for the inspection of large numbers of objects.

SUMMARY OF THE INVENTION

This object is achieved by a device of the type mentioned in the preamble which is characterized in that the device comprises a box with reflective walls which is positioned above the supporting surface and in which the light source and the observation means are accommodated.

The design according to the invention causes light which is emitted by the light source to be reflected by the reflective walls and then light which is reflected by the walls to be reflected again by the other walls. This results in a constantly recurring light source which creates uniform illumination of the objects without the need for complicated positioning of the light sources. In theory, a uniform light source which recurs infinitely on all sides would be produced if walls with a coefficient of reflection of 1 are used.

In a preferred embodiment of the invention, the supporting surface comprises a conveyor for conveying the objects through the box past the observation means, with the result that large numbers of objects per unit time can be observed by the observation means and a highly expedient arrangement is achieved.

The invention will be explained in more detail with reference to the drawing.

DETAILED DESCRIPTION OF PREFERRED EMBODIMENTS

Figure 1:
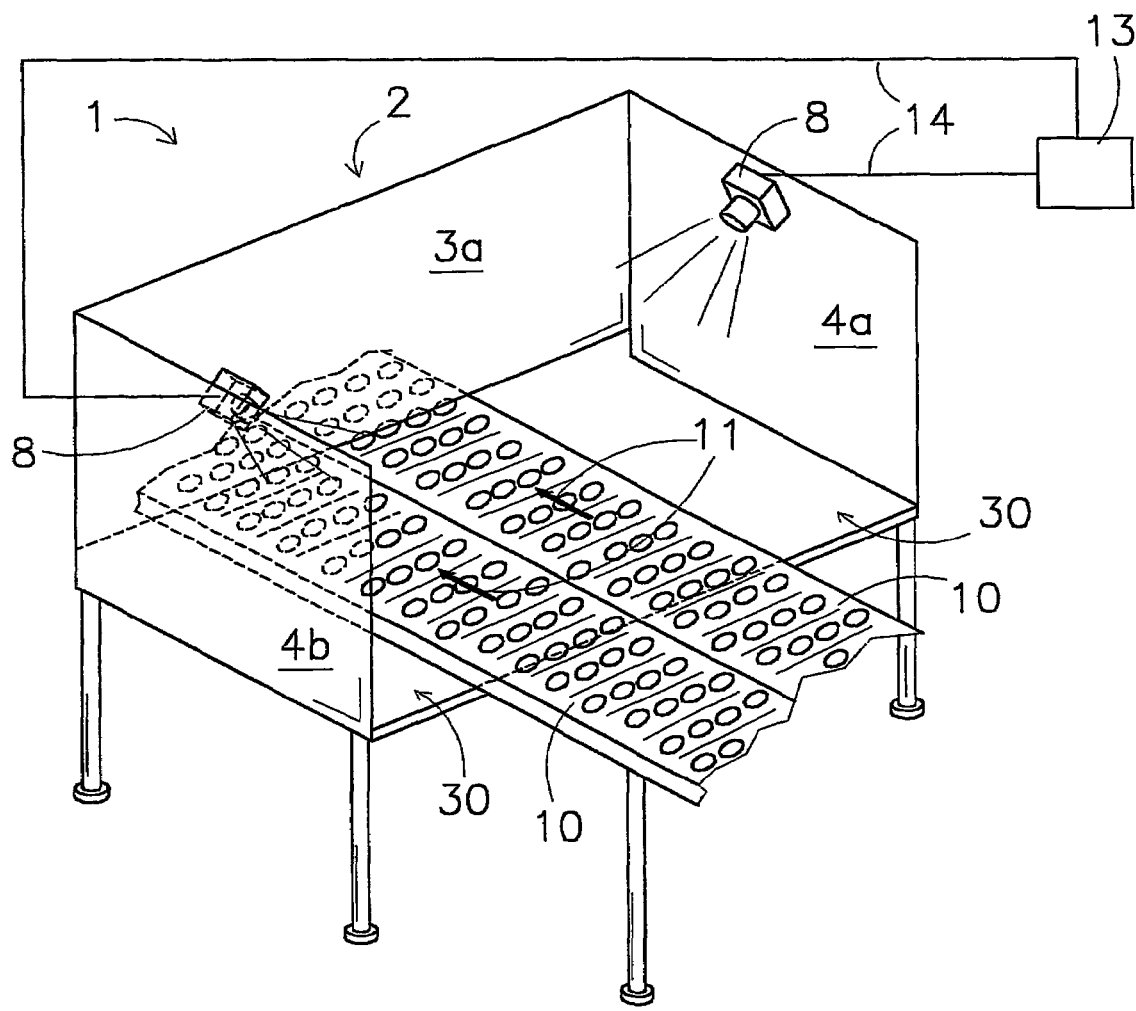
FIG. 1 shows a perspective view, obliquely from above, of a preferred embodiment of a device according to the invention.

FIG. 1 shows a perspective view of advice 1 according to the invention. The device 1 comprises a box 2 with four side walls 3a, 3b, 4a, 4b. For the sake of clarity, the view shown in FIG. 1 is cut away by virtue of the front side wall 3b being omitted from the figure. Furthermore, the box 2 has a top wall, which is likewise omitted from FIG. 1 for the sake of clarity. In the embodiment shown, the width of the side walls 3a and 3b is greater than that of the side walls 4a and 4b.

Figure 2:
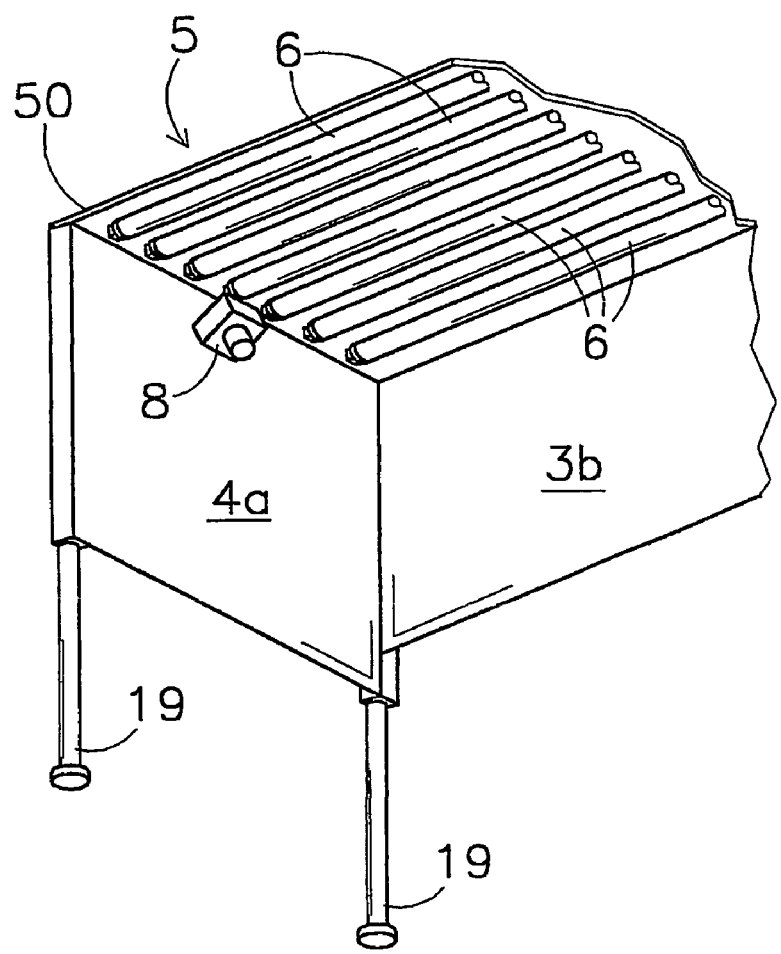
FIG. 2 shows a perspective view, obliquely from below, of a portion of the device shown in FIG. 1.
Figure 3:
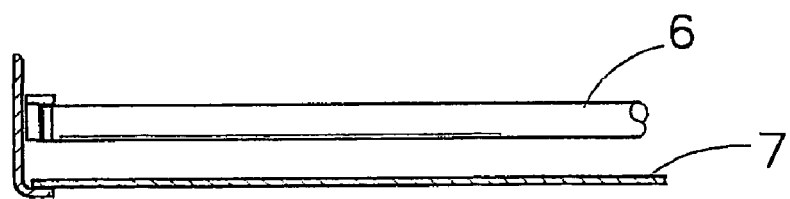
FIG. 3 shows a cross section through a portion of the top side of the device shown in FIG. 1.

FIG. 2 shows a perspective view, obliquely from below, of the box 2 illustrating the side walls 3b and 4a. Furthermore, the top side 5 of the box is visible. Strip Lights 6 are arranged at regular intervals on the top side 5 of the box 2. In FIG. 2, the strip lights 6 are not covered. However, it is preferable for them to be covered by one or more diffuser plates 7 made from a matt transparent material, for example milky-white glass or plastic, as shown in FIG. 3. The strip lights 6 together form a light source which is not completely uniform but is made more uniform by the diffuser plate 7. These diffuser plates 7 form the top wall of the box 2. This arrangement of the strip lights 6 and the diffuser plate 7 means that the box 1, on the top side 5, has a light source with a substantially even light plane directed towards the inside of the box 2. This even light plane emits light downwards in all directions in a uniform way.

Figure 4:
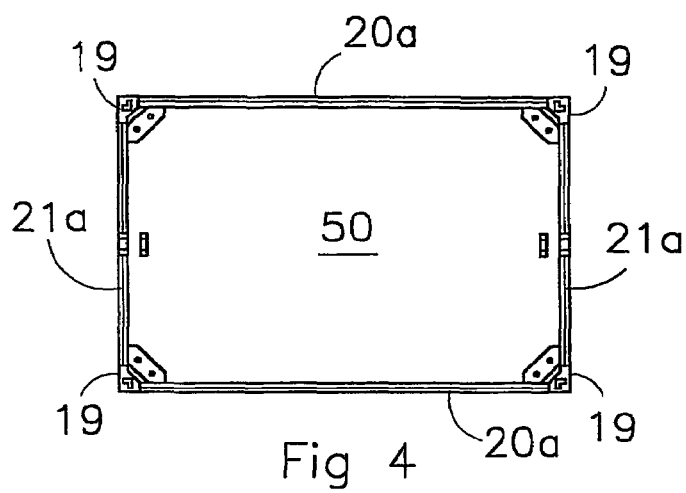
FIG. 4 shows a cross section through the box of the device shown in FIG. 1, on line IV-IV in FIG. 5.
Figure 5:
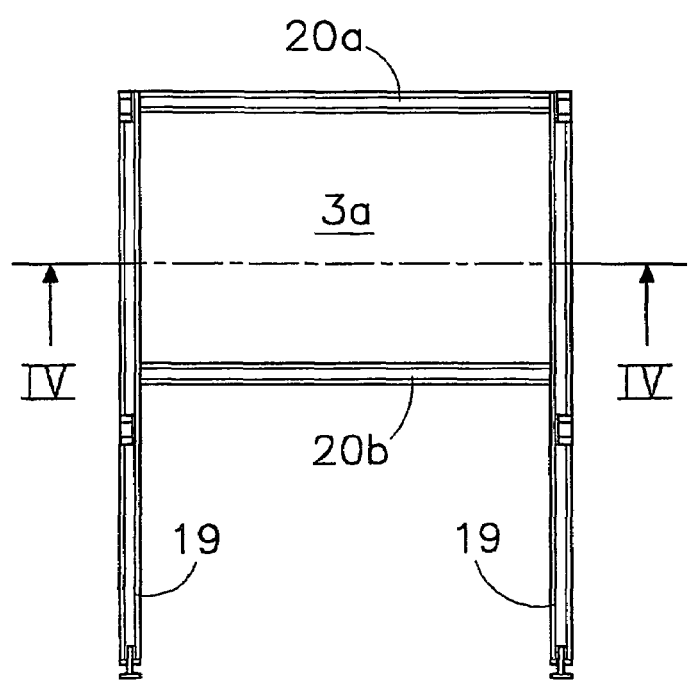
FIG. 5 shows a side view of the box of the device shown in FIG. 1.
Figure 6:
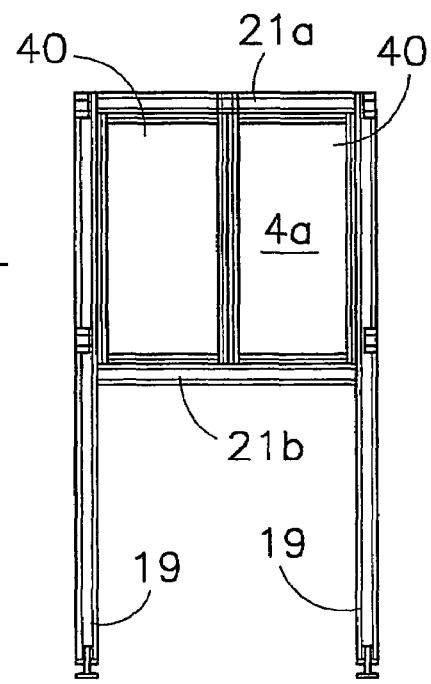
FIG. 6 shows a front side view of the box of the device shown in FIG. 1.

FIGS. 4-6 show a preferred embodiment of the box 2. This box 2 comprises a frame which is composed of four upright section pieces 19 and top and bottom longitudinal section pieces 20a, 20b, as well as top and bottom transverse section pieces 21a and 21b, the longitudinal and transverse section pieces 20a, 20b, 21a, 21b being positioned perpendicular to the upright section pieces 19 and connecting the latter to one another. The upright section pieces 19 are designed to be supported by a floor surface. The side walls 3a, 3b, 4a and 4b of the box 2 are secured to the frame, as shown in FIGS. 5 and 6. In the preferred embodiment shown, the side faces 4a and 4b are formed from two parts, as illustrated in FIG. 6. These two parts are formed as access doors 40 which are hinged or slideably secured to the frame. Access to the inside of the box 2 can be gained via the access doors 40. The side faces are produced from metal sheet and have a mirroring surface, preferably with a high coefficient of reflection, facing towards the inside of the box 2. It is preferable for the coefficient of reflection to be 0.8 or higher. The side faces of the box 2 according to the invention thus function as mirrors. This is different than known inspection devices, in which the inner side of the box reflects the light diffusively, e.g. by applying white matt paint to the inner side.

A top cover plate 50 is fitted to the top side of the frame, as can be seen from FIG. 4. The strip lights 6 are arranged beneath this top cover plate 50 (cf. FIG. 2). It is preferable for the cover plate 50 to be made from reflective material, in order for light which is radiated upwards from the strip lights 6 to be reflected downwards towards the diffuser plate 7. This results in an even more even light plane at the top side 5 of the box 2.

Light which is emitted by the strip lights 6 via the diffusor plate 7 into the box is reflected by the reflective walls 3a, 3b, 4a and 4b. Also, light reflected by the respective side walls 3a, 3b, 4a, 4b is reflected again by the other side walls 3a, 3b, 4a, 4b. As a result of the mirroring side walls a light source recurring as a mirror image on all sides is produced. The higher the coefficient of reflection of the walls, the more frequently the light source will recur on all sides. In theory, in the case of walls with a coefficient of reflection of 1, a constantly recurring light source would be produced. The illumination from all sides means that the illumination of a separate object 12 is no longer dependent on the position of the said object 12 on the conveyor 10 and therefore means that a plurality of objects can be placed next to one another on a conveyor and can be illuminated equally well.

One or more conveyors 10 pass through the bottom of the box 2. In the situation shown in FIG. 1, the box 2 is located above two conveyors 10 which are arranged parallel and next to one another and extend parallel to the side walls 4a and 4b. Of course, the box 2 may also be used with more or fewer conveyors 10 or, for example, with a stationary supporting surface. Therefore, the conveying direction of the conveyors 10 extends substantially parallel to the longitudinal direction of the box 2, i.e. the width of the side faces 4a and 4b. The combined width of the adjacent conveyors 10 is preferably less than the width of the box 2, i.e. the width of the side faces 3a and 3b, with the result that there is a space 30 next to the conveyors 10 in the box 2, in which a person can stand in order, for example, to eliminate any faults. Objects 12 which are to be inspected, for example eggs or fruit, can be conveyed through the box 2 in rows on the conveyors 10, in the direction illustrated by the arrows 11.

The light source which recurs via the reflective walls 3a, 3b, 4a, 4b provides uniform illumination of the substantially spherical objects 12 from all sides, irrespective of whether the object 12 is positioned in the centre or in the vicinity of the edge of the conveyor. This is expedient for inspection of the objects 12 by means of a camera and optical data processing, as explained below.

Furthermore, a camera 8 is arranged above the conveyors 10 at the top side 5 of the box 2 in the vicinity of each of the side walls 4a and 4b. The cameras 8 each have an observation field which extends over the entire width of the conveyors 10 arranged next to one another. The observation field preferably extends at least over a centre section of the length of the box 2, since in the centre section the illumination strength is most even from all sides. Therefore, the objects 12 passed through the observation field of the cameras 8 by the conveyor 10 can be observed obliquely from above from two sides by means of the cameras 8, resulting in a good view of the objects.

It is preferable for there to be openings in the diffuser plate 7 or for there to be two diffuser plates 7, with a gap between them, through which the cameras, as it were, can look at the conveyor. It is preferable for the lens of the cameras 8 to be positioned in the plane of the diffuser plate 7. This prevents the diffuser plate 7 from restricting the observation area of the cameras 8. However, should the cameras 8 project beneath the diffuser plate 7, they would allow a shadow to form in the box 2.

Figure 7:
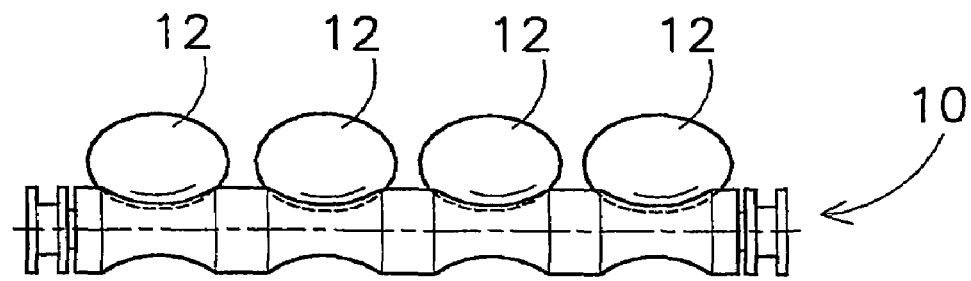
FIG. 7 shows a front view of a conveyor for eggs.
Figure 8:
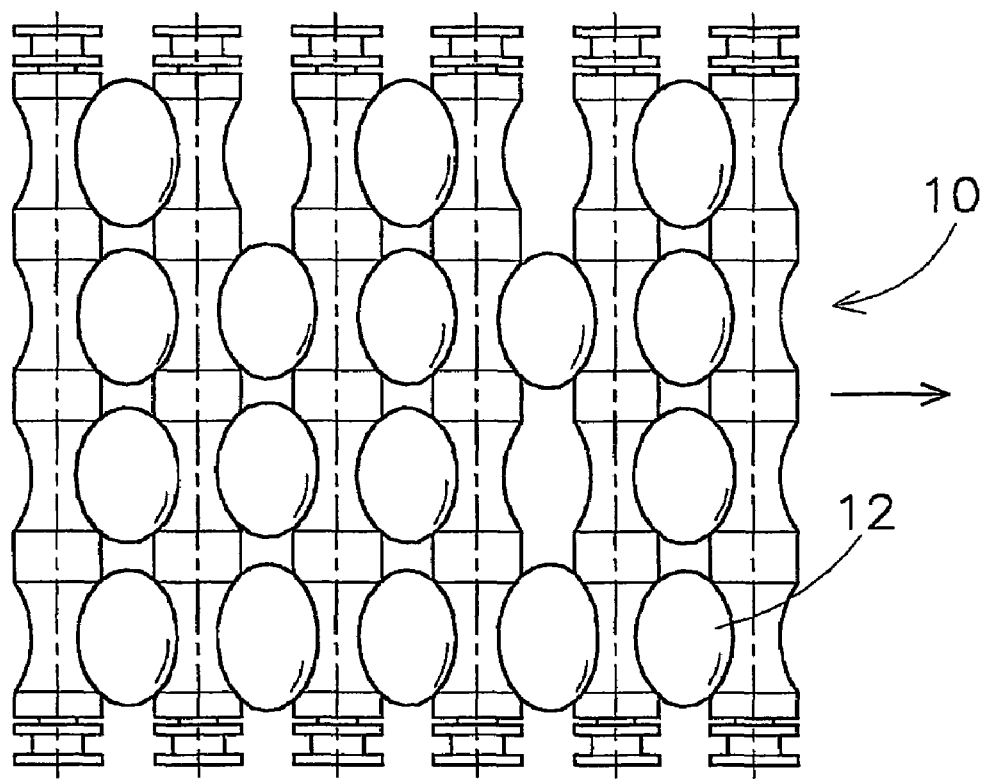
FIG. 8 shows a plan view of the conveyor shown in FIG. 7.

It is preferable for the conveyor 10 to be designed in such a manner that the objects 12 execute a rolling movement as they are being conveyed. This type of conveyor is known from the prior art, and FIGS. 7 and 8 show an example of a conveyor of this type for eggs. The rolling motion of the objects 12 allows each camera 8 to observe each object 12 over its entire circumference.

The cameras 8 are preferably in each case coupled to a computer 13 via a data link 14. The images recorded by each camera 8 can be fed to the computer 13, where they can be combined in a manner which is known per se with the aid of image-processing software and are compared with predetermined reference values. If an object 12 has, for example, a soiled surface, this can be determined in the computer 13 as a result of the colour or pattern of spots of the object 12 deviating excessively from the reference. The computer 13 can record the position of the deviating object 12 on the conveyor 10 and emit a control signal to a removal device (not shown) located further downstream in order for objects which deviate excessively to be automatically removed from the conveyor 10. It should be noted that this automatic selection and removal may also be effected in other ways and is no way essential to the invention.

What is claimed is:

1. Inspection device for inspecting eggs or fruit with a substantially spherical surface, comprising:

a conveyor adapted to convey a plurality of eggs or fruit placed next to each other in a direction transverse to the conveying direction, at least one camera for observing the eggs or fruit on the conveyor, a box having a mirroring surface which is positioned above the conveyor and in which the at least one camera is accommodated, the mirroring surface consisting essentially of four reflective side wall mirrors having a coefficient of reflection of at least 0.8, where the four reflective side wall mirrors are side walls that define the box, and a light source which is accommodated in the box opposite the conveyor for illuminating the eggs or fruit from above, the light source having a substantially even light plane directed towards the inside of the box, and which light source, as a result of the mirroring side walls, recurs on all sides so as to provide uniform illumination of the eggs or fruit on the conveyor from all sides.

2. Inspection device according to claim 1, wherein the box is substantially rectangular and has a top cover plate joining the four reflective side walls.

3. Inspection device according to claim 1, wherein the reflective side walls are made from metal.

4. Inspection device according to claim 1, wherein the light source is arranged on the top side of the box.

5. Inspection device according to claim 4, wherein the light source has a uniform radiation plane.

6. Inspection device according to claim 4, wherein the light source comprises one or more lamps which are distributed substantially uniformly.

7. Inspection device according to claim 5, wherein the light source is arranged beneath the top cover plate above one or more diffusor plates.

8. Inspection device according to claim 1, wherein the device has at least two cameras which are arranged on opposite sides of the box.

9. Inspection device according to claim 1 wherein the device comprises a computer which is coupled to the at least one camera in order to compare the observations with predetermined reference values for automatic selection of the eggs or fruit.

10. Inspection device according to claim 1, wherein the conveyor is designed in such a manner that the eggs or fruit execute a rolling movement as they are being conveyed.

* * * * *